United States Patent
Zhao et al.

(10) Patent No.: US 11,324,781 B2
(45) Date of Patent: May 10, 2022

(54) APPLICATION OF GENETICALLY ENGINEERED BACTERIA VNP20009-M IN PREPARING DRUG FOR TREATING MALIGNANT SARCOMA

(71) Applicant: GUANGZHOU SINOGEN PHARMACEUTICAL CO., LTD, Guangzhou (CN)

(72) Inventors: Allan Zijian Zhao, Guangzhou (CN); Yan Lin, Guangzhou (CN); Sujin Zhou, Guangzhou (CN); Fanghong Li, Guangzhou (CN)

(73) Assignee: GUANGZHOU SINOGEN PHARMACEUTICAL CO., LTD., Guangzhou (CN)

(*) Notice: Subject to any disclaimer, the term of this patent is extended or adjusted under 35 U.S.C. 154(b) by 260 days.

(21) Appl. No.: 16/497,825

(22) PCT Filed: Mar. 29, 2018

(86) PCT No.: PCT/CN2018/081116
§ 371 (c)(1),
(2) Date: Sep. 26, 2019

(87) PCT Pub. No.: WO2018/177375
PCT Pub. Date: Oct. 4, 2018

(65) Prior Publication Data
US 2020/0023020 A1    Jan. 23, 2020

(30) Foreign Application Priority Data
Apr. 1, 2017 (CN) .......................... 201710216811.9

(51) Int. Cl.
| | | |
|---|---|---|
| *A61K 35/74* | (2015.01) | |
| *A61P 35/00* | (2006.01) | |
| *A61K 9/00* | (2006.01) | |
| *C12N 15/74* | (2006.01) | |
| *C12N 1/20* | (2006.01) | |
| *C12R 1/42* | (2006.01) | |

(52) U.S. Cl.
CPC ............ *A61K 35/74* (2013.01); *A61K 9/0019* (2013.01); *A61P 35/00* (2018.01); *C12N 1/205* (2021.05); *C12N 15/74* (2013.01); *C12R 2001/42* (2021.05)

(58) Field of Classification Search
None
See application file for complete search history.

(56) References Cited

FOREIGN PATENT DOCUMENTS

| | | | | |
|---|---|---|---|---|
| CN | 103961721 A | * | 8/2014 | ............. A61K 48/00 |
| WO | WO-03/063593 A1 | * | 8/2003 | ............. A01N 63/00 |

OTHER PUBLICATIONS

Kreis and Hession, "Biological effects on enzymatic deprivation of L-methionine in cell culture and an experimental tumor", Cancer Research 33: 1866-1869 (August) (Year: 1973).*
Google English translation of CN103961721A downloaded Sep. 27, 2021 (Year: 2021).*

* cited by examiner

*Primary Examiner* — Anand U Desai
(74) *Attorney, Agent, or Firm* — Jun He Law Offices P.O.; James J. Zhu

(57) ABSTRACT

Provided is application of genetically engineered bacteria VNP20009-M in preparation of drugs for preventing and treating malignant sarcoma.

14 Claims, 4 Drawing Sheets

APPLICATION OF GENETICALLY ENGINEERED BACTERIA VNP20009-M IN PREPARING DRUG FOR TREATING MALIGNANT SARCOMA

CROSS-REFERENCE TO RELATED APPLICATIONS

The present application is the national phase of International Application PCT/CN2018/081116, filed Mar. 29, 2018, which claims the benefit of Chinese Patent Application No. CN 201710216811.9, filed Apr. 1, 2017, the disclosure of which is incorporated herein by reference in the entirety.

FIELD OF THE INVENTION

The present invention belongs to the technical field of genetic engineering drugs and particularly relates to new application of genetically engineered bacteria VNP20009-M in preparation of a drug for preventing and treating malignant sarcoma.

BACKGROUND

Cancers have become an important cause of human death with cancer incidence rates increasing by 33% from 2005 to 2015. The World Cancer Report 2014 published by the World Health Organization (WHO) predicts a rapid increase in world cancer cases, from 14 million in 2012 to 19 million in 2025 year by year and reaching 24 million by 2035.

Sarcomas are malignant tumors derived from mesenchymal tissues (including connective tissues and muscles) and mainly occur at fat, fascias, muscles, fibers, lymph, blood vessels, periosteum, and both ends of long bones. Each sarcoma has different histological and biological characteristics and different local infiltration, hematogenous and lymphatic metastasis tendencies, wherein the sarcoma metastasis to the lungs is more common.

Clinical manifestations of the sarcomas are mass and syndromes occur when the mass enlarges to press surrounding tissues. An incidence of the sarcomas is very low with an annual incidence of 2.4-5 cases per 100,000 people, accounting for about 1% of adult malignant tumors, 15% of childhood malignant tumors, but 2% of all cancer-related mortality. Due to a large number of sarcoma subtypes and various biological behaviors, diagnosis is relatively difficult. A disease state is often late when the sarcoma is discovered, and about ⅓-½ of patients die from sarcoma recurrence and metastasis. Development of current medical means for treatment of advanced sarcomas is always stagnant; and chemotherapy is still a standard treatment method. For example, doxorubicin-containing treatment is a standard program; and an overall survival period of treated patients is only 12-16 months. Overall, a 5-year survival rate of early patients is about 60%-80%, and the 5-year survival rate of advanced patients is less than 20%.

The prior art shows that methionine dependence is a characteristic of most tumor cells, which is manifested by excessive demands for methionine by the tumor cells and cell proliferation is inhibited when culture is conducted in a methionine removed or precursor homocysteine substituted culture medium; while in the presence of the methionine, the cells can grow normally, including more than ten malignant tumor cells of prostate cancer, breast cancer, lung cancer, etc. However, there is no methionine dependence in normal cells. The method that causes methionine deficiency mainly includes removing the methionine from diet or decomposing the methionine by using methioninase. However, limiting intake of the methionine in diet alone has a limited effect on lowering the methionine level, and long-term limiting on the methionine intake can cause body malnutrition and metabolic disorders. Compared to the diet-limited methionine intake, the use of the methioninase does not cause excessive metabolic problems and has an anti-tumor effect.

*Salmonella* is a group of Gram-negative and invasive intracellular facultative anaerobic bacteria parasitized in intestines of humans and animals. Among the *salmonella*, a known bacterium strain VNP20009 is a vector with high tumor targeting properties, safety, and antitumor effects. The VNP20009 has significant tumor growth inhibition effects on various mouse solid tumor models of malignant melanoma, lung cancer, etc. Two phase I clinical studies conducted in the United States show that the VNP20009 can be used in the human body, has safety, but shows no antitumor effects.

SUMMARY

To this end, a technical problem to be solved by the present invention is to provide new application of genetically engineered bacteria VNP20009-M in preparation of a drug for preventing and treating malignant sarcoma.

In order to solve the above technical problem, the present invention discloses the application of the genetically engineered bacteria VNP20009-M in the preparation of the drug for preventing and treating the malignant sarcoma.

Further, the sarcoma comprises malignant sarcomas derived from mesenchymal tissues including connective tissues, muscles, etc.

Further, the sarcoma comprises those occurring at fat, fascias, muscles, fibers, lymph, blood vessels, periosteum, and both ends of long bones.

Further, the sarcoma comprises soft tissue sarcomas and osteosarcomas.

Among existing patients with the soft tissue sarcomas, undifferentiated pleomorphic sarcoma (UPS) is the most common, accounting for 25-35%; liposarcoma (LPS) is the second common, accounting for 25-30%; leiomyosarcoma (LMS) accounts for 12%; synovial sarcoma (SS) accounts for 10%; and malignant peripheral nerve sheath tumor (MPNST) accounts for 6%.

The osteosarcomas, also known as osteogenic sarcomas, occur mostly in adolescents or children under 20 years old. The osteosarcomas are developed from mesenchymal cell lines and the tumors grow rapidly due to direct or indirect formation of tumor osteoid tissues and bone tissues through a cartilage stage. The osteosarcomas are most common in pediatric bone malignant tumors which are about 5% of pediatric tumors.

The sarcoma comprises primary sarcomas, postoperative recurrent sarcomas, or sarcomas metastasized to other sites after surgery.

Further, the sarcoma is tumor metastasized to the lungs after the surgery of the malignant sarcomas.

Preferably, the genetically engineered bacteria VNP20009-M have a minimum effective administration dose of $6.4*10^7$ CFU/M$^2$.

Administration manners of the tumor prevention and treatment comprises various routes including but not limited to oral administration, local administration, injection administration (including but not limited to transvenous, peritoneal, subcutaneous, intramuscular, intratumoral administrations), etc.

As known in the prior art, the genetically engineered bacteria VNP20009-M of the invention are a known bacterium strain, and properties, shapes, and construction methods of the VNP20009-M are all as described in Chinese Patent No. CN105983103A.

The genetically engineered bacteria VNP20009-M are attenuated *Salmonella typhimurium* VNP20009 cloned with a L-methioninase gene.

Further, the genetically engineered bacteria VNP20009-M are attenuated *Salmonella typhimurium* VNP20009 carrying a plasmid, wherein the plasmid is cloned with the L-methioninase gene.

The genetically engineered bacteria VNP20009-M are constructed by subcloning the L-methioninase gene into the plasmid to obtain a L-methioninase expression plasmid, and electrotransforming the L-methioninase expression plasmid into the attenuated *Salmonella typhimurium* VNP20009.

The plasmid includes but is not limited to a pSVSPORT plasmid, a pTrc99A plasmid, a pcDNA3.1 plasmid, a pBR322 plasmid or a pET23a plasmid.

Most preferably, in the construction process of the genetically engineered bacteria VNP20009-M, when the pSVS-PORT plasmid is selected, the L-methioninase gene is subcloned into the plasmid to obtain the L-methioninase expression plasmid, and then the L-methioninase expression plasmid is electrotransformed into the attenuated *Salmonella typhimurium VNP*20009 to obtain the genetically engineered bacteria.

Wherein, electrotransformation is conducted under a voltage of 2,400 V, a resistance of 400Ω, a capacitance of 25 μF and a discharge time of 4 ms.

The present invention also discloses application of the genetically engineered bacteria VNP20009-M in preparation of a methioninase agent.

The present invention discloses the new application on the existing basis of the genetically engineered bacteria VNP20009-M for treating the malignant sarcoma. The genetically engineered bacteria VNP20009-M can effectively kill tumor cells, eliminate tumor lesions, have better killing effects and better therapeutic effects for primary sarcomas, recurrent tumor after surgery and tumor cells metastasized to other sites after the surgery of the malignant sarcomas, and especially have relatively good killing effects on tumors metastasized to the lungs after the surgery of the soft tissue sarcomas; and besides, the genetically engineered bacteria have no obvious toxic and side effects on the human body and provide safe and effective new methods for the treatment of the malignant sarcomas.

BRIEF DESCRIPTION OF THE DRAWINGS

In order to make the content of the present invention easier to understand, the present invention will be further described in detail below with reference to the embodiments of the present invention accompanying with the drawings, wherein.

DETAILED DESCRIPTION

Example 1 Construction of Genetically Engineered Bacteria VNP20009-M

The construction method and processes of the genetically engineered bacterium VNP20009-M of the present invention are described in the examples of the Chinese Patent No. CN105983103A.

(1) Construction of Plasmid Expressing L-Methioninase Gene

The L-methioninase (GenBank: L43133.1) gene was synthesized and subcloned into a pUC57 plasmid (GenScript). The pUC57 plasmid subcloned with the L-methioninase gene was then subcloned into a pSVSPORT plasmid (Invitrogen) by Kpn I and Hind III enzyme cutting sites to obtain a pSVSPORT-L-methioninase expression plasmid. The specific construction processes are as follows:

the pSVSPORT plasmid was subjected to Kpn I and Hind III double enzyme cutting. An enzyme cutting system contained 2 μg of plasmid DNA, 3 μL of 10*buffer, 1.5 μL of Kpn I enzyme, 1.5 μL of Hind III enzyme, and ddH$_2$O added to supplement sufficiently a volume to 30 μL, and incubated in warm bath at 37° C. for 3 h. Then the enzyme cutting system was separated by electrophoresis in 1% agarose gel. A DNA band of 4.1 kb was cut out and purified by a gel recovery and purification kit.

The DNA fragment of a L-methioninase coding region was obtained by whole-gene synthesis. The obtained DNA fragment was subcloned into the pUC57 plasmid (GenScript). The pUC57 plasmid subcloned with the DNA fragment was subjected to the Kpn I and Hind III double enzyme cutting using an enzyme cutting system containing 3 μg of plasmid DNA, 3 μL of 10*buffer, 1.5 μL of Kpn I enzyme, 1.5 μL of Hind III enzyme, and ddH$_2$O added to supplement sufficiently a volume to 30 μL, which was incubated in warm bath at 37° C. for 3 h. The enzyme cutting system was then separated by electrophoresis in 1% agarose gel. A DNA band of 1.2 kb was cut out and purified by a gel recovery and purification kit.

The pSVSPORT (Kpn I/Hind III) and the DNA fragment of the L-methioninase coding region (Kpn I/Hind III) were ligated with a ligation reaction containing 2 μL of the vector, 6 μL of the inserting fragments and 1 μL of T4 DNA ligase and incubated in warm bath at 16° C. for 16 h.

The ligation product was transformed into competent cells of *E. coli* DH5α (Takara). A tube of 50 μL of DH5α competent cells was placed on ice. After the ice was melt, 5 μL of the above-mentioned ligation product was added into the DH5α competent cells with slight flipping to mix. The mixture was incubated on ice for 30 min before heat shock at 42° C. for 60 s and then incubated on ice for 2 min. 500 μL of LB liquid medium without antibiotics was added to the mixture and incubated at 37° C. for 1 h with shaking, after which the material was spread on an ampicillin-containing LB culture medium plate and cultured overnight.

Figure 1:
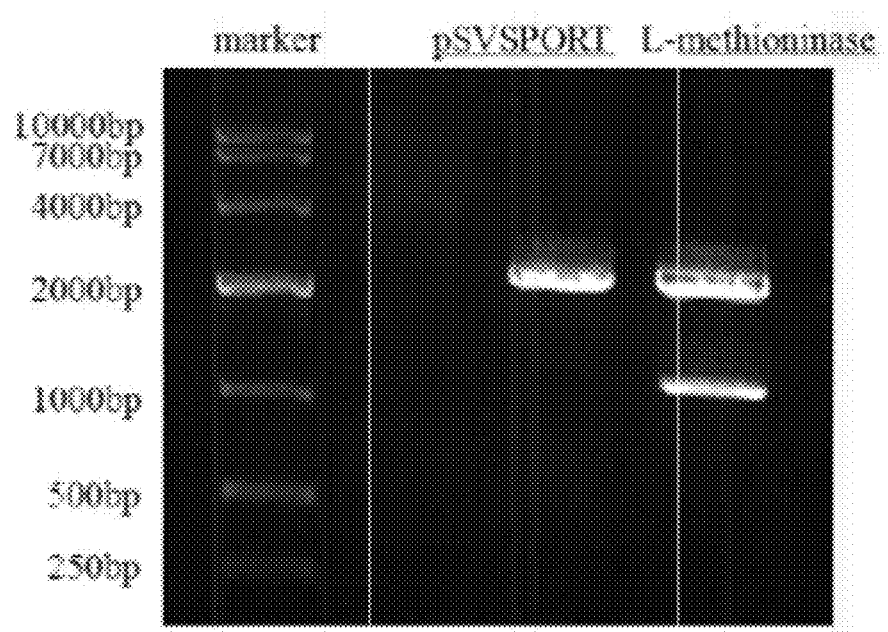
FIG. 1 is a diagram of 1% agarose gel electrophoresis to identify the plasmid pSVSPORT-L-methioninase by enzyme digestion.

After clones were grown, single colonies were picked into 3 mL of ampicillin-containing LB culture liquid, incubated in a shaker at 37° C. for 16 h. Plasmid DNA was extracted and identified by Kpn 1 and Hind 111 enzyme digestion. As shown in FIG. 1, the positive clone had two DNA bands of 4.1 kb and 1.2 kb. Sequencing confirmed that the sequences of the positive clones are completely correct.

(2) Constructions of VNP20009 Bacterium Carrying a Plasmid and VNP20009 Bacterium Carrying a Plasmid Cloned with a L-Methioninase Gene pSVSPORT and pSVSPORT-L-methioninase expression plasmids were respectively electrotransformed into the VNP20009 bacterium strain (YS1646, ATCC No. 202165) which were respectively named as VNP20009-V and VNP20009-M. The specific construction processes are as follows:

Competent bacteria VNP20009 were placed on ice, after the ice was melted, the competent bacteria VNP20009 were transferred to a pre-cooled electric rotating cup, 2 μL of the plasmid was added into the electric rotating cup, slight flipping and uniform mixing were conducted, and incubation was conducted on ice for 1 min. The electric rotating cup was put into an electric rotating instrument, and conditions were set as a voltage of 2,400 V, a resistance of 400Ω, a capacitance of 25 μF and a discharge time of 4 ms. 1 mL of a SOC culture medium was added immediately after electric shock, and gentle and even mixing was conducted. Shaking culture is conducted at 37° C. for 1 h; and after a pipettor was used to precipitate and blow the bacteria evenly, the bacteria were applied on an ampicillin-containing resistant LB-O culture medium plate. The plate was then put in an incubator for culture at 37° C. for 16 h. After the VNP20009-V and VNP20009-M were cultured with the LB-O, the plasmid was extracted and identified by enzyme cutting to be correct.

Figure 2:
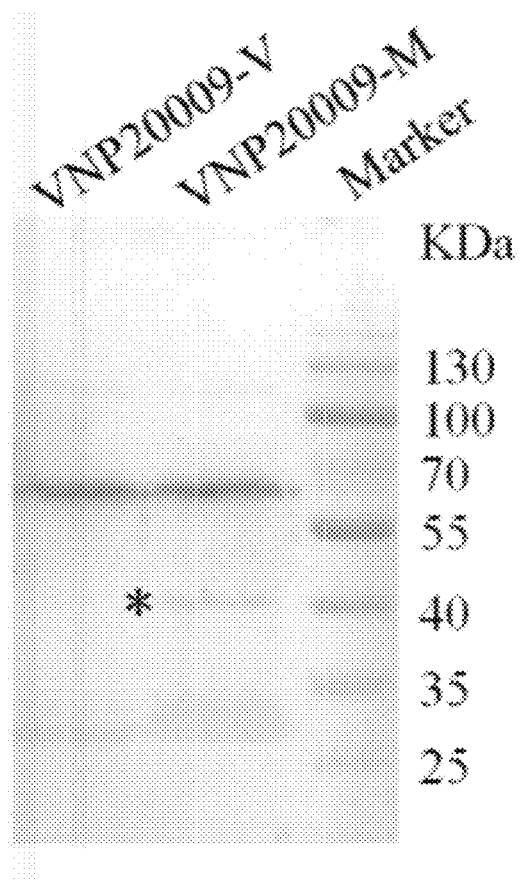
FIG. 2 is a diagram showing the results of methioninase expression identified by Western blot according to the present invention.

$1 \times 10^8$ of *salmonella* were taken, proteins were extracted by a protein lysate, 10% SDS-PAGE electrophoresis was conducted, then electrotransformation to a PVDF membrane in an ice bath under stable pressure was conducted, after BSA room temperature sealing was conducted for 1 h, TBST rinsing was conducted for 3*5 min, a rabbit anti-L-methioninase antibody was added (1:1000), and incubation was conducted overnight at 4° C. The TBST rinsing was conducted for 3 times with 5 min each time, then a HRP-labeled anti-rabbit secondary antibody (1:10000) was added, incubation was conducted at room temperature for 1 h, the TBST rinsing was conducted for 3 times with 5 min each time, and ECL chemiluminescence developing was conducted. The results are shown in FIG. 2, a specific band was observed at a molecular weight of about 43 kD, indicating that the expression level of the L-methioninase was significantly increased in the VNP20009-M compared with the VNP20009 and VNP20009-V.

Figure 3:
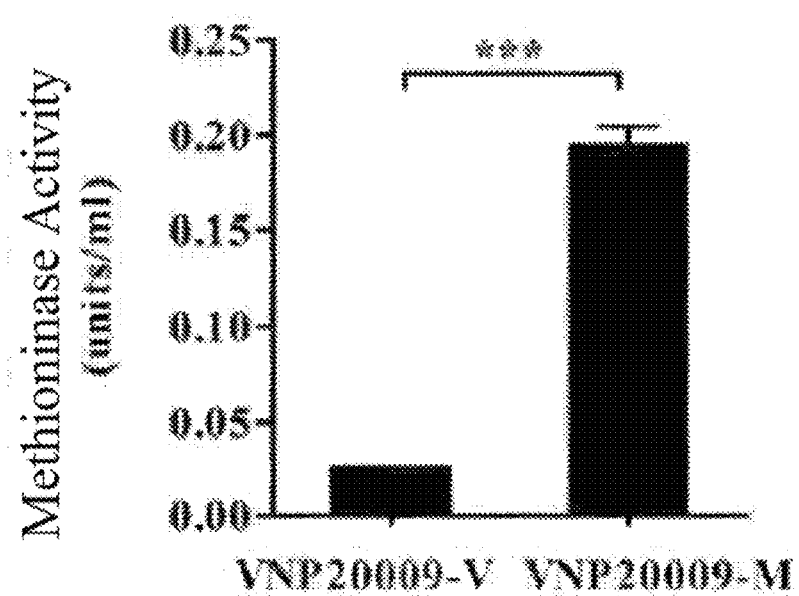
FIG. 3 is a diagram showing the results of detecting methioninase activity in *salmonella* according to the present invention.

L-methionine and pyridoxal were respectively mixed with the VNP20009-V and VNP20009-M bacteria. After incubation was conducted at 37° C. for 10 min, termination was conducted with 50% trichloroacetic acid, centrifugation was conducted, a supernatant was taken, the supernatant was mixed fully and evenly with 3-methyl-2-benzothiazolinone hydrazone hydrochloride hydrate (MBTH), after incubation was conducted at 50° C. for 30 min, absorbance at 320 nm was measured, and the amount of enzyme used for catalytic conversion of 1 μmol of α-ketobutyric acid per minute was defined as 1 enzyme activity unit. The results show (as shown in FIG. 3) that the activity of the methioninase in the *salmonella* VNP20009-M was 10 times higher than that of VNP20009-V.

Thus, the constructed genetically engineered *salmonella* VNP20009-M has a relatively high methioninase activity and can be used for preparation of a methioninase agent.

Example 2 Effect of Genetically Engineered Bacteria VNP20009-M for Treating Soft Tissue Sarcomas 1) Past Medical History and Diagnosis A clinical male patient, 64 years old, with a left leg mass, was identified as spindle cell sarcoma by needle biopsy at Nanjing Drum Tower Hospital. The patient was then subjected to tumor resection. The tissues were taken to be subjected to pathologic analysis, showing tumor cells SMA (−), DES (−), MyoD1 (−), FN(+), STAT6 (−), CD34 (−), S100 (−), CKpan (−), EMA (−), Vimentin (++), in combination with HE slices; and the results were in line with malignant fibrous histiocytoma.

A regular follow-up CT re-examination showed space-occupying right lung upper lobe soft tissues; and needle biopsy pathology showed the spindle cell sarcoma. According to the patient's past treatments and related examinations, recurrence of lung metastasis after the surgery of the spindle cell sarcoma was diagnosed.

2) Treatment Plan

The genetically engineered bacteria VNP20009-M diluted with 250 mL of physiological saline were intravenously administered to the body at a dose of $6.4*10^7$ CFU/M$^2$ at an interval of 1 week; and a total of 5 times of infusion was conducted.

3) Efficacy 3.1 Changes of Tumor Sizes

Figure 4:
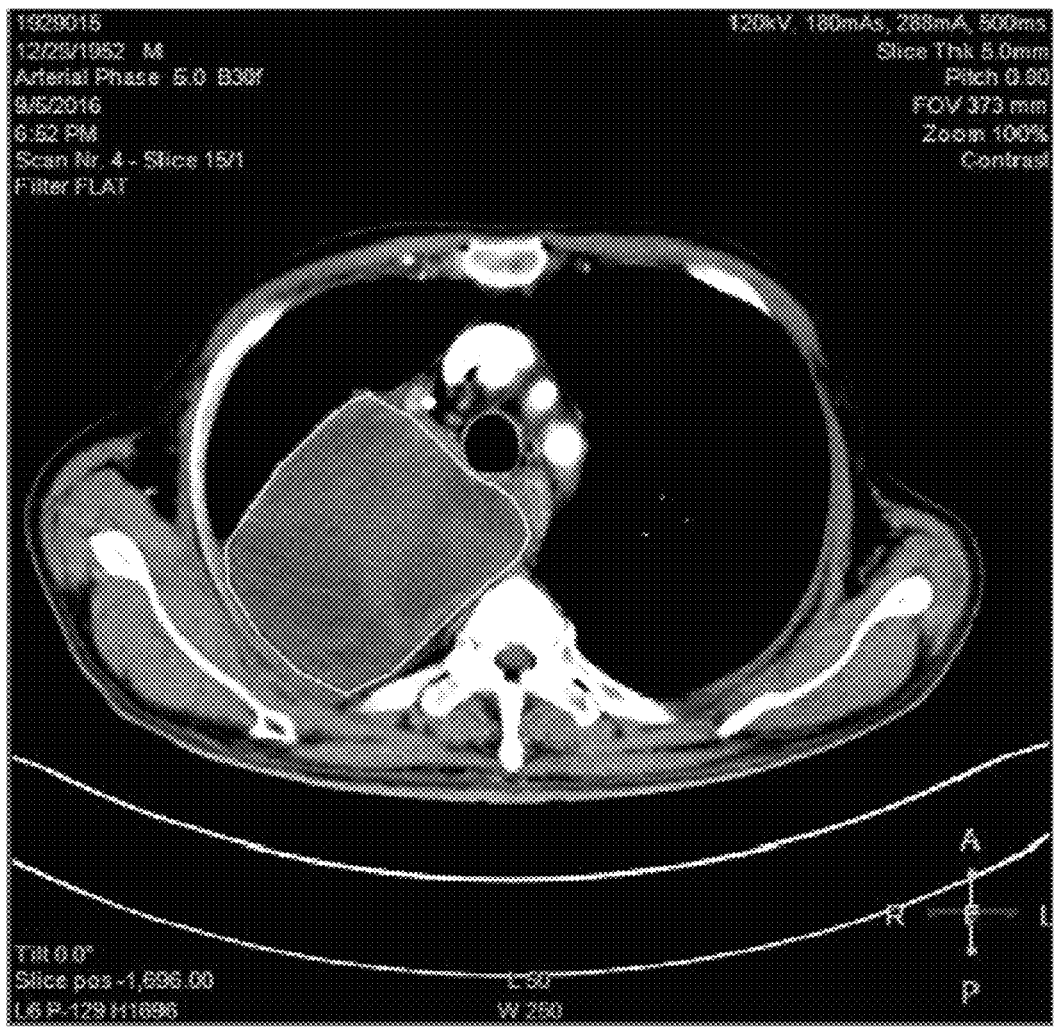
FIG. 4 shows the chest CT examination results of a lesion condition of the patient before treatment in Example 2.
Figure 5:
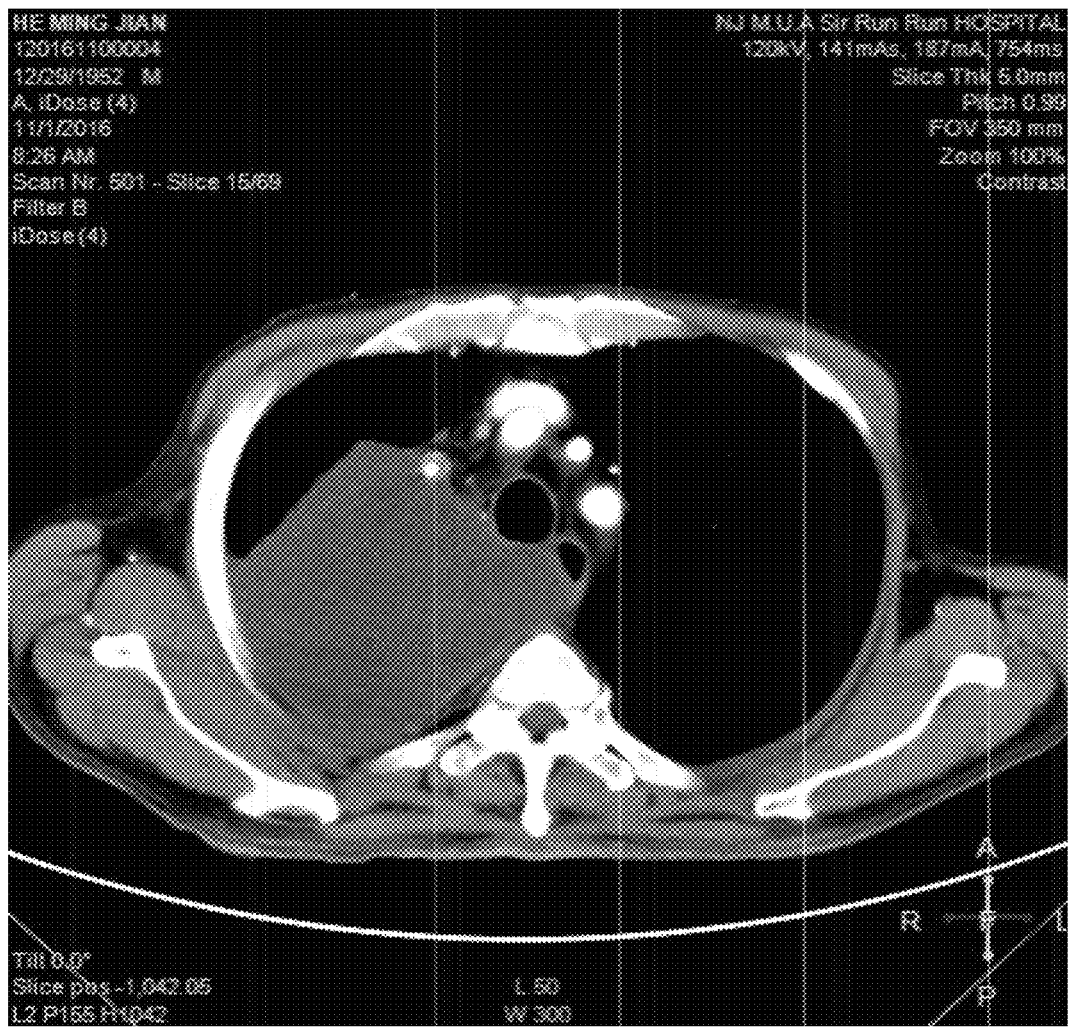
FIG. 5 is the result of a chest CT examination of the patient after 4 weeks of the treatment in Example 2.

A chest CT examination before the treatment showed a size of the right lung upper lobe lesion was approximately 18*10*10 cm (as shown in FIG. 4). After 4 weeks of the treatment, the CT examination showed that the size of the right lung upper lobe lesion was approximately 17*10*10 cm (as shown in FIG. 5), and there was no significant change in the tumor size compared with that before the treatment.

3.2 Changes Inside the Tumor

Before the treatment, a CT image showed flaky liquefied necrosis inside the lung lesion. As shown in FIG. 4, the inside of the lesion circled by white lines presented uneven colors, the darker regions indicated that the cells here had become necrotic and the brighter regions indicated living cells. After 4 weeks of the treatment, the CT image showed a uniform structure inside the lesion (as shown in FIG. 5) with a CT value of approximately 10 HU. The CT value indicated substance density; and when the CT value was lower than 20 HU, the substance was liquid, suggesting that the tumor cells in the region were basically necrotic and presented liquid. Therefore, the tumor cells of the patient with the sarcoma were rapidly necrotic and liquefied after the treatment with the VNP20009-M. However, since the lesion was in the body, the liquid could not be extracted, so that shrinking of the lesion was not observed.

3.3 Side Effects

On the day of each treatment, 5-6 hours after the infusion, the patient had a highest fever of about 39.6° C. and restored normal body temperature by physical cooling. Other than that, there was no other abnormal feeling. During the treatment, various indicators of liver and kidney functions were examined; and the results were shown in Table 1 below. Detection results showed that the various indicators of the patient body were basically similar to those before the treatment. The above results indicate that the VNP20009-M produced no extra toxic and side effects to the patient.

TABLE 1

Various indicator data of the patient body

| Indicators | Reference value | Before the treatment | 1 week after the treatment | 4 weeks after the treatment | 8 weeks after the treatment |
|---|---|---|---|---|---|
| Alanine aminotransferase | 0-33 U/L | 20 | 26 | 16 | 19 |
| Aspartate aminotransferase | 0-32 U/L | 16 | 20 | 13 | 21 |
| Total bilirubin | 0-21 μmol/L | 8.3 | 9.5 | 11.7 | 15 |
| Alkaline phosphatase | 35-104 U/L | 71 | 91 | 96 | 140 |
| Lactic dehydrogenase | 109-245 U/L | 158 | 160 | 135 | 127 |
| Albumin | 35-52 g/L | 27 | 30 | 29 | 24 |
| Urea nitrogen | 2.86-8.21 mmol/L | 4.36 | 2.41 | 3.2 | 2.23 |
| Creatinine | 59-104 μmol/L | 55 | 57 | 51 | 52 |
| Potassium | 3.5-5.1 mmol/L | 3.1 | 4.14 | 4.01 | 3.56 |
| Sodium | 136-145 mmol/L | 138 | 134 | 136 | 137 |
| Blood platelet | 125-350 10*9/L | 118 | 153 | 155 | 103 |

The above data prove that the VNP20009-M can effectively kill the malignant sarcoma cells and eliminate the tumor lesions, and has no severe toxic and side effects on the human body.

It is apparent that the above-described embodiments are merely illustrative of the examples and are not intended to limit the embodiments. Other variations or modifications of the various forms may also be made by those of ordinary skill in the art in light of the above description. There is no need and no way to exhaust all of the embodiments. And the obvious variations or modifications derived therefrom are still in the protection scope created by the present invention.

The invention claimed is:

1. A method for treating malignant sarcoma, the method comprising administering a therapeutically effective amount of genetically engineered bacterium to a human having malignant sarcoma, wherein the genetically engineered bacterium is attenuated *Salmonella typhimurium* VNP20009 cloned with a L-methioninase gene.

2. The method of claim 1, wherein the malignant sarcoma is derived from a mesenchymal tissue.

3. The method of claim 2, wherein the mesenchymal tissue is a connective tissue or muscle.

4. The method of claim 1, wherein the malignant sarcoma occurs at fat, fascias, muscles, fibers, lymph, blood vessels, periosteum, and both ends of long bones.

5. The method of claim 1, wherein the malignant sarcoma is a soft tissue sarcoma or bone sarcoma.

6. The method of claim 1, wherein the malignant sarcoma is a primary sarcoma, a postoperative recurrent sarcoma, or a sarcoma metastasized to other sites after surgery.

7. The method of claim 6, wherein the malignant sarcoma is a sarcoma metastasized to lungs after surgery.

8. The method of claim 1, wherein the genetically engineered bacterium is administered at a dose of at least $6.4 \times 10^7$ CFU/M$^2$.

9. The method of claim 1, wherein the genetically engineered bacterium is administered once a week.

10. The method of claim 1, wherein the genetically engineered bacterium is administered orally, locally or via injection.

11. The method of claim 10, wherein the genetically engineered bacterium is administered via transvenous injection, peritoneal injection, subcutaneous injection, intramuscular injection, or intratumoral injection.

12. The method of claim 1, wherein the genetically engineered bacterium carries a plasmid which is cloned with the L-methioninase gene.

13. The method of claim 1, wherein the plasmid is a pSVSPORT plasmid, a pTrc99A plasmid, a pcDNA3.1 plasmid, a pBR322 plasmid or a pET23a plasmid.

14. The method of claim 1, wherein the genetically engineered bacterium is constructed by: subcloing the L-methioninase gene into the plasmid, then electrotransforming the plasmid to attenuated *Salmonella typhimurium* VNP20009.

* * * * *